United States Patent
Wollenweber et al.

(10) Patent No.: US 7,853,314 B2
(45) Date of Patent: Dec. 14, 2010

(54) METHODS AND APPARATUS FOR IMPROVING IMAGE QUALITY

(75) Inventors: Scott David Wollenweber, Waukesha, WI (US); Alex Ganin, Whitefish Bay, WI (US); Mark K. Limkeman, Brookfield, WI (US); Charles William Stearns, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1976 days.

(21) Appl. No.: 10/371,552

(22) Filed: Feb. 21, 2003

(65) Prior Publication Data

US 2004/0167387 A1 Aug. 26, 2004

(51) Int. Cl.
A61B 6/00 (2006.01)

(52) U.S. Cl. .................. 600/436; 600/425; 382/131; 250/363.03

(58) Field of Classification Search ........... 600/407, 600/425, 436; 250/363.03
See application file for complete search history.

(56) References Cited

U.S. PATENT DOCUMENTS

| | | | | |
|---|---|---|---|---|
| 5,323,007 A | * | 6/1994 | Wernick et al. | 250/363.03 |
| 5,457,724 A | * | 10/1995 | Toth | 378/4 |
| 5,850,486 A | * | 12/1998 | Maas et al. | 382/294 |
| 6,026,142 A | | 2/2000 | Gueziec et al. | |
| 6,094,467 A | * | 7/2000 | Gayer et al. | 378/4 |
| 6,201,888 B1 | | 3/2001 | Kalvin | |
| 6,236,705 B1 | * | 5/2001 | Stergiopoulos et al. | 378/8 |
| 6,292,578 B1 | * | 9/2001 | Kalvin | 382/131 |
| 6,396,898 B1 | * | 5/2002 | Saito et al. | 378/19 |
| 6,449,330 B1 | * | 9/2002 | Li et al. | 378/4 |
| 6,462,342 B1 | | 10/2002 | Stearns | |
| 7,020,315 B2 | * | 3/2006 | Vaisburd et al. | 382/131 |
| 2002/0081008 A1 | * | 6/2002 | Wollenweber | 382/131 |
| 2002/0122575 A1 | * | 9/2002 | Vaisburd et al. | 382/131 |
| 2002/0186809 A1 | * | 12/2002 | Flohr et al. | 378/4 |
| 2003/0004405 A1 | | 1/2003 | Townsend et al. | |
| 2004/0136501 A1 | * | 7/2004 | Boyd et al. | 378/210 |

FOREIGN PATENT DOCUMENTS

WO WO 00/75691 * 12/2000

* cited by examiner

Primary Examiner—Ruth S Smith
Assistant Examiner—Joseph Santos
(74) Attorney, Agent, or Firm—Armstrong Teasdale LLP

(57) ABSTRACT

A method for retrospectively correcting data prior to image reconstruction using an imaging system, wherein the method includes acquiring a first sinogram of a first slice of an object at a first axial field of view and a second sinogram of the first slice of the object at a second axial field of view different than the first axial field of view, determining at least one boundary of the object in the first sinogram and the second sinogram at the first slice, measuring a shift between the first sinogram and the second sinogram using the determined boundaries, and generating a corrected image using the measured shift.

27 Claims, 5 Drawing Sheets

METHODS AND APPARATUS FOR IMPROVING IMAGE QUALITY

BACKGROUND OF THE INVENTION

This invention relates generally to imaging systems, and more particularly, to methods and apparatus for retrospectively correcting for deficiencies in image quality of images from imaging systems.

At least one known PET transmission scan is acquired using a rotating source of dual-511 keV gamma rays, such as the Ge-68 rod sources implemented on imaging systems, such as a PET Advance™ system from General Electric Medical Systems, Waukesha, Wis. At least one known PET imaging system is commonly used in whole-body acquisition mode to acquire adjacent axial fields-of-view (AFOVs) with a small amount of overlap. The acquisition mode is a step-and-shoot style and not continuous bed motion over a 15 cm AFOV. Post-acquisition reconstruction is then performed and the images are placed into an imageset. This imageset can then be viewed in using an orthogonal reformat tool, which allows viewing of a whole-body study in a more intuitive manner than simply viewing the native transaxial slices. Image quality problems can occur when combining the discrete sets of images together when the images were acquired using a step-and-shoot imaging system with an extended axial FOV. For example, if a cradle performing the axial translation either drives along an axis that is not the scanner axis or has a "differential sag," i.e. varying curvature of a cradle top as a function of the cradle extension, then the image can include discontinuities. These discontinuities can be seen in a coronal view of the images as horizontal lines or in a sagittal view of the images as a "saw tooth" type effect. Such discontinuities reduce the quality of the imageset and hence the clinical confidence in the study.

BRIEF SUMMARY OF THE INVENTION

In one aspect, a method for retrospectively correcting data prior to image reconstruction using an imaging system is provided. The method includes acquiring a first sinogram of a first slice of an object at a first axial field of view and a second sinogram of the first slice of object at a second axial field of view different than the first axial field of view, determining at least one boundary of the object in the first sinogram and the second sinogram at the first slice, measuring a shift between the first sinogram and the second sinogram using the determined boundaries, and generating a corrected image using the measured shift.

In another aspect, an imaging system including a radiation source, a radiation detector, and a computer operationally coupled to the radiation source and the radiation detector is provided. The computer is configured to acquire a first sinogram of an object at a first axial field of view and a second sinogram of the object at a second axial field of view different than the first axial field of view, determine at least one boundary of the object in the first sinogram and the second sinogram, measure a shift between the first sinogram and the second sinogram using the determined boundaries, and generate a corrected image using the measured shift.

In a further aspect, a computer readable medium encoded with a program is provided. The program is configured to instruct a computer to acquire a first sinogram of a first slice of an object at a first axial field of view and a second sinogram of the first slice of object at a second axial field of view different than the first axial field of view, determine at least one boundary of the object in the first sinogram and the second sinogram, measure a shift between the first sinogram and the second sinogram using the determined boundaries, and generate a corrected image using the measured shift.

DETAILED DESCRIPTION OF THE INVENTION

Figure 1:
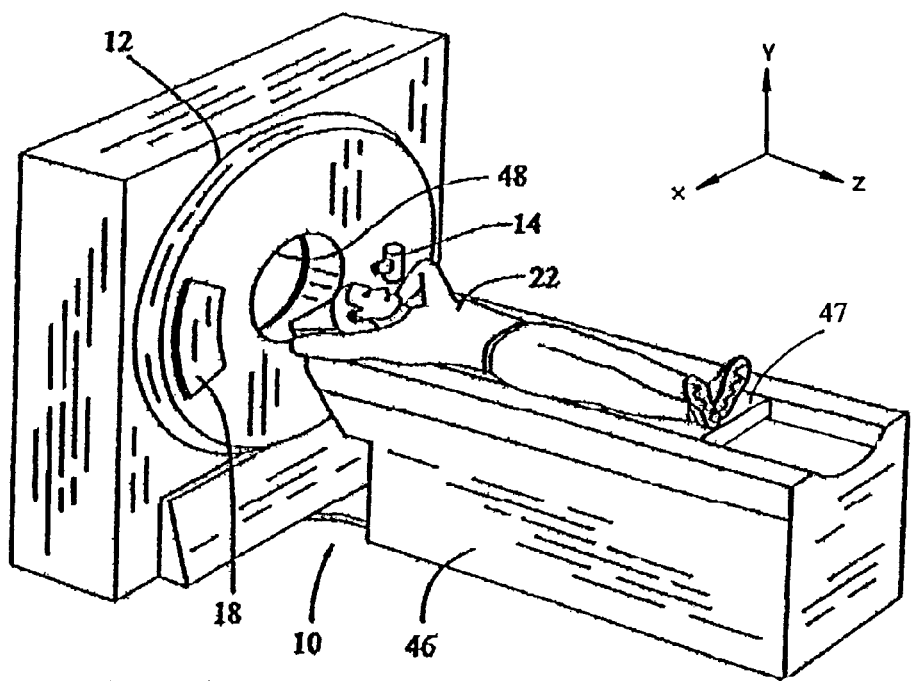
FIG. 1 is a pictorial view of an imaging system.

In some known CT imaging system configurations, an X-ray source projects a fan-shaped beam which is collimated to lie within an X-Y plane of a Cartesian coordinate system and generally referred to as an "imaging plane". The X-ray beam passes through an object being imaged, such as a patient. The beam, after being attenuated by the object, impinges upon an array of radiation detectors. The intensity of the attenuated radiation beam received at the detector array is dependent upon the attenuation of an X-ray beam by the object. Each detector element of the array produces a separate electrical signal that is a measurement of the beam intensity at the detector location. The intensity measurements from all the detectors are acquired separately to produce a transmission profile.

In third generation CT systems, the X-ray source and the detector array are rotated with a gantry within the imaging plane and around the object to be imaged such that the angle at which the X-ray beam intersects the object constantly changes. A group of X-ray attenuation measurements, i.e., projection data, from the detector array at one gantry angle is referred to as a "view". A "scan" of the object comprises a set of views made at different gantry angles, or view angles, during one revolution of the X-ray source and detector.

In an axial scan, the projection data is processed to reconstruct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display. Current PET scanners incorporate a process similar to that found in CT, in that a map of the object attenuation can be generated. A common method to perform this attenuation measurement includes use of rotating rod sources containing positron-emitting radionuclides. The rods rotate outside the patient bore, but inside the diameter of the PET detector ring. Annihilation events occurring in the rods can send one photon into a near-side detector while the pair photon traverses the object of interest in a manner similar to the CT X-ray. The data found from this method contains essentially the same information as that found from the CT method except for the statistical quality of the resultant data. In the rotating rod case, the statistical quality is orders of magnitude inferior to most common CT scans. For the PET purpose, data acquired in this manner is used to correct for the attenuation seen in the object by the 511 keV photons, which is often the most substantial correction performed on the PET data. The resultant PET images can be formed into quantitative units of radioactivity concentration following this correction.

To reduce the total scan time of a CT scan, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

At least some CT systems are configured to also perform Positron Emission Tomography (PET) and are referred to as PET-CT systems. Positrons are positively charged electrons (anti-electrons) that are emitted by radionuclides that have been prepared using a cyclotron or other device. The radionuclides most often employed in diagnostic imaging are fluorine-18 ($^{18}$F), carbon-11 ($^{11}$C), nitrogen-13 ($^{13}$N), and oxygen-15 ($^{15}$O). Radionuclides are employed as radioactive tracers called "radiopharmaccuticals" by incorporating them into substances such as glucose or carbon dioxide. One common use for radiopharmaceuticals is in the medical imaging field.

To use a radiopharmaceutical in imaging, the radiopharmaceutical is injected into a patient and accumulates in an organ, vessel, or the like, which is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism, fatty acid metabolism, and protein synthesis. Hereinafter, in the interest of simplifying this explanation, an organ to be imaged including a vessel will be referred to generally as an "organ of interest" and the invention will be described with respect to a hypothetical organ of interest.

After the radiopharmaceutical becomes concentrated within an organ of interest and while the radionuclides decay, the radionuclides emit positrons. The positrons travel a very short distance before they encounter an electron and, when the positron encounters an electron, the electron-positron pair annihilates. The result is a pair of nearly collinear photons, or gamma rays. This annihilation event is characterized by two features that are pertinent to medical imaging and particularly to medical imaging using positron emission tomography (PET). First, each gamma ray has an energy of approximately 511 keV upon annihilation. Second, the two gamma rays are directed in nearly opposite directions.

In PET imaging, if the general locations of annihilations can be identified in three dimensions, a three dimensional image of radiopharmaceutical concentration in an organ of interest can be reconstructed for observation. To detect annihilation locations, a PET camera is employed. An exemplary PET camera includes a plurality of detectors and a processor that, among other things, includes coincidence detection circuitry.

The coincidence circuitry identifies essentially simultaneous pulse pairs that correspond to detectors that are essentially on opposite sides of the imaging area. Thus, a simultaneous pulse pair indicates that annihilation has occurred somewhere along a straight line between an associated pair of detectors. Over an acquisition period of a few minutes, millions of annihilations are recorded, each annihilation being associated with a unique detector pair. After an acquisition period, recorded annihilation data can be used via any of several different well known image reconstruction methods to reconstruct the three dimensional radioactivity concentration image of the organ of interest.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
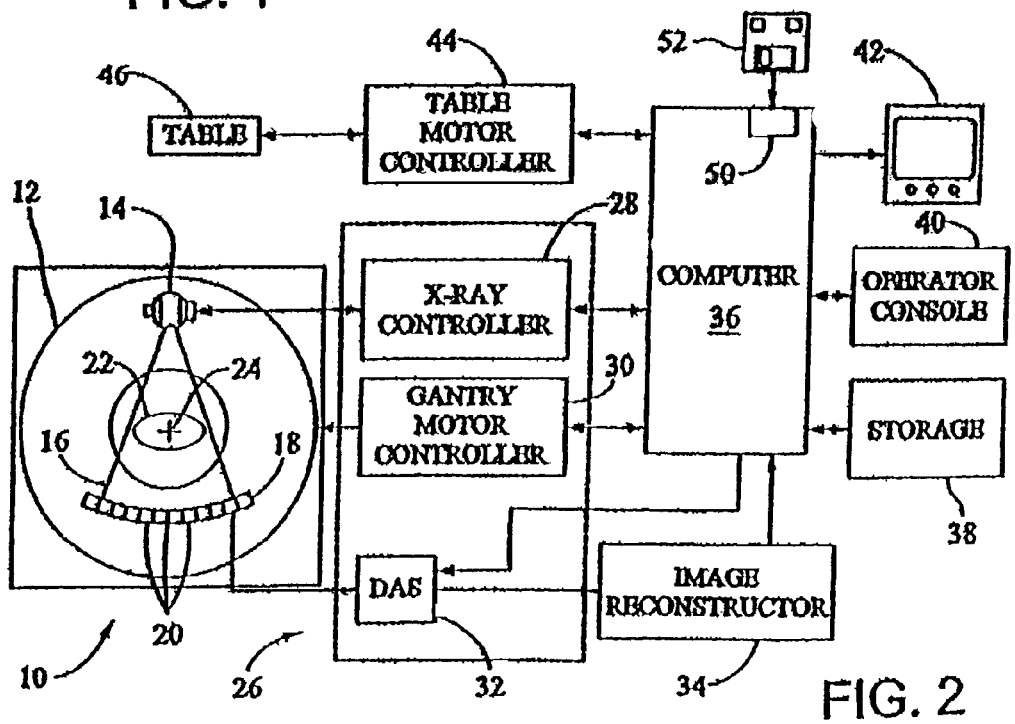
FIG. 2 is a block schematic diagram of the system illustrated in FIG. 1.

Referring to FIGS. 1 and 2, a multi-slice scanning imaging system, for example, a Positron Emission Tomography/Computed Tomography (PET-CT) imaging system 10, is shown as including a gantry 12 representative of a "third generation" CT imaging system in combination with PET circuitry. Gantry 12 has an X-ray source 14 that projects a beam of X-rays 16 toward a detector array 18 on the opposite side of gantry 12. Detector array 18 is formed by a plurality of detector rows (not shown) including a plurality of detector elements 20 which together sense the projected X-rays that pass through an object, such as a medical patient 22. Each detector element 20 produces an electrical signal that represents the intensity of an impinging X-ray beam and hence allows estimation of the attenuation of the beam as it passes through object or patient 22. During a scan to acquire X-ray projection data, gantry 12 and the components mounted thereon rotate about a center of rotation 24. FIG. 2 shows only a single row of detector elements 20 (i.e., a detector row). However, a multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of X-ray source 14 are governed by a control mechanism 26 of PET-CT system 10. Control mechanism 26 includes an X-ray controller 28 that provides power and timing signals to X-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized X-ray data from DAS 32 and performs high-speed image reconstruction. The reconstructed image is applied as an input to a computer 36 which stores the image in a storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. PET-CT system 10 also includes a plurality of PET detectors. The PET detectors and detector array 18 both detect radiation and are both referred to herein as radiation detectors. In one embodiment, PET-CT system 10 is a Discovery LS PET-CT system commercially available from General Electric Medical Systems, Waukesha Wis., and configured as herein described, including the ability to acquire the attenuation information from both the CT and the rotating rod source(s) incorporated into the PET gantry, as described previously. In another embodiment, system 10 performs at least one of a CT and PET imaging, but not both. In an alternative embodiment, imaging system 10 is an imaging modality other than CT and PET.

Although the specific embodiment mentioned above refers to a third generation CT system and a PET imaging system, the methods described herein equally apply to fourth generation CT systems (stationary detector—rotating X-ray source), fifth generation CT systems (stationary detector and X-ray source) or other PET-only or nuclear systems wherein a rod-source attenuation measurement system is incorporated.

Additionally, although the herein described methods are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center. The benefits also accrue to micro PET and CT systems that are sized to study lab animals as opposed to humans.

Figure 3:
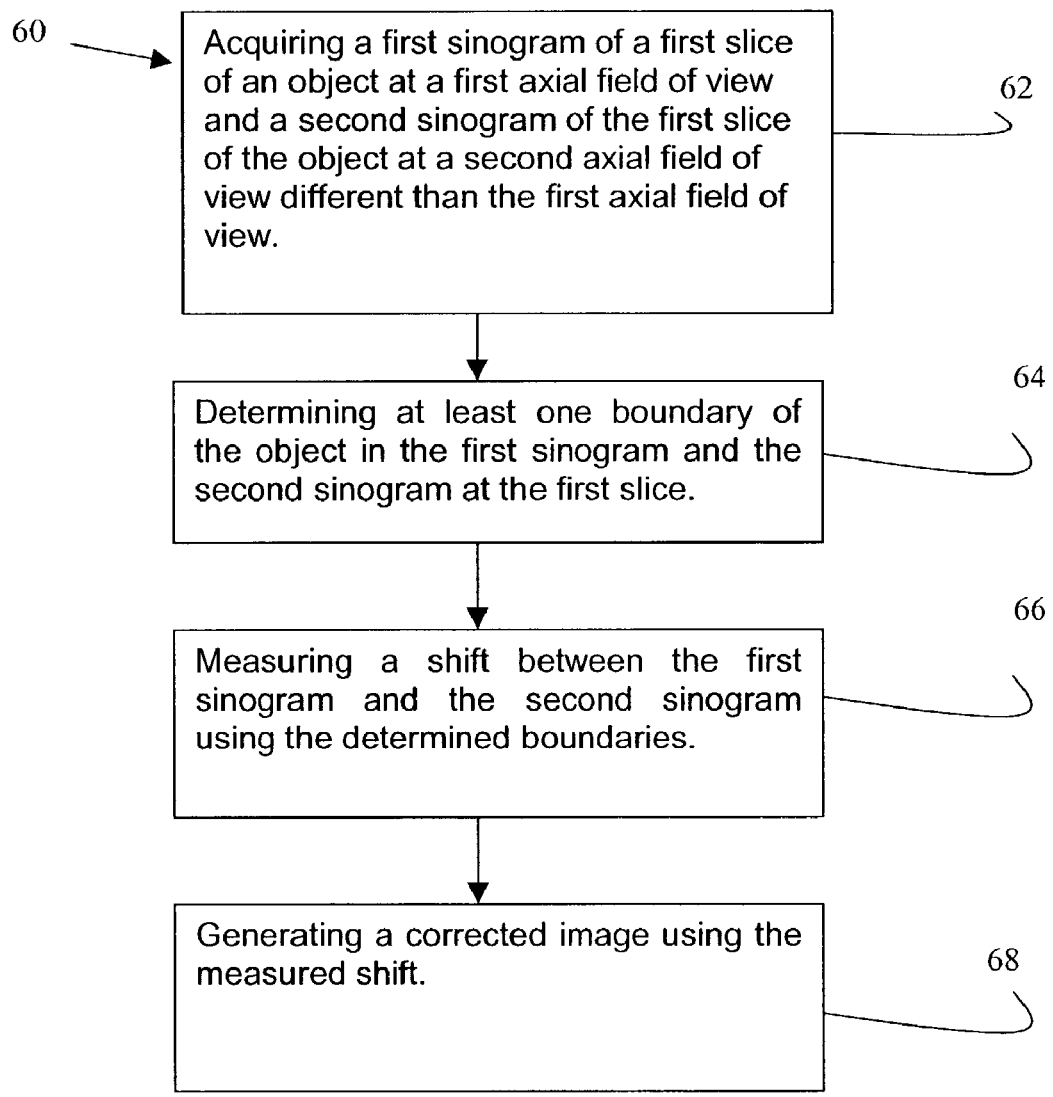
FIG. 3 is a method for retrospectively correcting an image using an imaging system.

FIG. 3 is a method 60 for retrospectively correcting an image using imaging system 10. Method 60 includes acquiring 62 a first sinogram of a first slice of an object at a first axial field of view in the scanning system and a second sinogram of the same slice of the object at a second axial field of view different than the first axial field of view, determining 64 at least one boundary of the object in the first sinogram and the second sinogram at the first slice, measuring 66 a shift between the first sinogram and the second sinogram using the determined boundary, and generating 68 a corrected image using the measured shift.

The method of correction described in FIG. 3 can apply to a non step-and-shoot system, since the idea is to re-align many acquisitions of the same physical slice location of the imaged object by computing the shift between the acquisitions (of the same physical slice of object). The overall idea is that these acquisitions were acquired with the same input signal, but the alignment may change as a function of cradle extension. Given the assumption that the object didn't change between the various acquisitions (2 or more) of the slice location, one can compute the shift using FIG. 3.

In use, system 10 is employed in different types of scans including a whole body study where the acquisition mode is a step and shoot style wherein data is acquired in a plurality of Z locations but cradle 47 is stationary during each data acquisition. In other words, cradle 47 is translated in the Z direction only between acquisitions. The data at each Z location is called a frame. For several reasons, sequential frames overlap. That is, a first frame including a plurality of slices of data corresponding to a plurality of detector rows is acquired at a first Z location, then cradle 47 is moved less than a detector width to a second Z location, and a second frame including a plurality of slices corresponding to the detector rows is acquired at the second Z location. Because cradle 47 is indexed less than the detector width, both the first and second frames contain at least one slice for the same body location. In other words, one section of the imaged object is seen in two different axial fields of views (overlap slices) wherein the field of views are separated in Z by a difference less than the detector width. If sag exists then there will be a difference between the sinograms corresponding to the different slices, as is shown in FIGS. 4-6.

In the exemplary embodiment, method 60 includes estimating a shift of cradle 47 in an X direction (yaw), and estimating a shift of cradle 47 in a Y direction (sag) at frame boundaries that include overlap slices by determining a lower and an upper bound using thresholding methods going across specified rows in the sinogram. Once these shifts are measured from the two PET emission sinograms, an assumption of linear change over slice location is used to deduce offsets for each slice in an AFOV. Correction for the shift is then applied during image reconstruction by making the back-projector and forward-projector (required for iterative reconstruction) knowledgeable of the intended center for the projection. Proper weighting during forward projection is typically maintained since data in corresponding overlap slices does not necessarily carry the same weight due to differences in slice sensitivity (for PET). In another embodiment, the PET transmission sinogram is used to calculate the shift(s).

The shift calculation is calculable in a variety of ways. One embodiment uses a two-step process parameterized by a cutoff and backoff. The first step is to generate a cutoff value. The cutoff value is a pre-determined percentage of a maximum or mean value for the pixels in a row of the sinogram. As referred to herein, the sinogram is a single sinogram of the first and second sinograms combined, and a row of the sinogram is a row in the first sinogram and a corresponding row in the second sinogram such that, when the first sinogram and the second sinogram are combined into the single sinogram, the corresponding rows in the first and second sinograms are a single row in the combined sinogram. For example, a row of the sinogram is examined for a maximum intensity value and then a cutoff value is set to be 60% of the maximum value. Alternatively a percentage other than 60% is used. Also, in one embodiment, the maximum value is not used, rather a mean is calculated for all the pixels in a row and a percentage of the mean is used as the cutoff value. In other embodiments, the cutoff value is determined in another way. Irrespective of how the cutoff value is determined, the cutoff value is used as a threshold. For example, a row of the sinogram is examined from the left side moving right until a pixel is found to be larger than the cutoff, this pixel location is set as the left boundary of the object being scanned. The process is repeated for the right side moving left, and a right side boundary is set. By setting boundaries for two sinograms, and then comparing the boundaries between the acquisitions of the same physical slice of object, one can measure shift which indicates sag (assuming the object did not change shape between the acquisitions). In one embodiment, a back-off is employed wherein the back-off is the amount of pixels "stepped-back" from the identified boundary to ensure being the identified boundary is outside the object. Although shift in both X and Y can be found using a plurality of locations (vertical) of the sinogram, it is computationally easier to use certain locations for determining shift in X and Y. For example, shifts in X are more easily calculated using the beginning and ending of the sinogram, while shifts in Y are more easily calculated using the middle of the sinogram. By knowing the construction of the sinogram based on the physical location of detectors, sinogram rows where the x and y shifts can most reliably be estimated can be defined. For prototyping, rows 0-6 and 330-335 (of a 336-angle sinogram) were used to measure x-shift while rows 162-173 were used to estimate y-shift.

Figure 4:
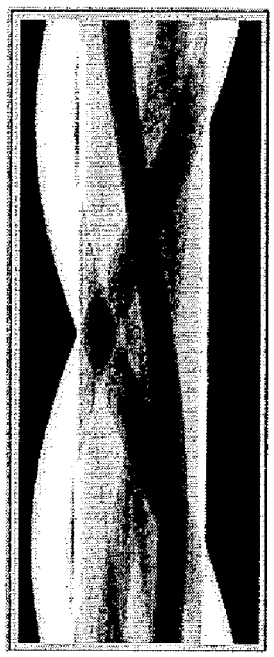
FIG. 4 is an attenuated PET emission sinogram that is not shifted.
Figure 5:
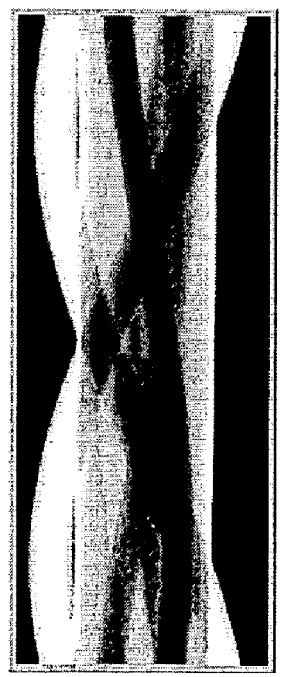
FIG. 5 is an attenuated PET emission sinogram that is shifted by 1 mm in a Y direction.
Figure 6:
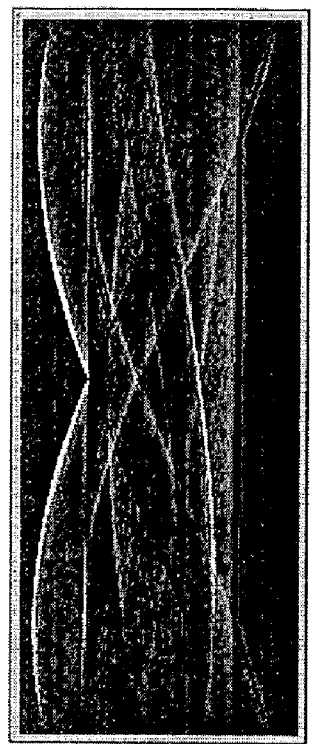
FIG. 6 is a difference sinogram between the data shown in FIGS. 4-5.
Figure 7:
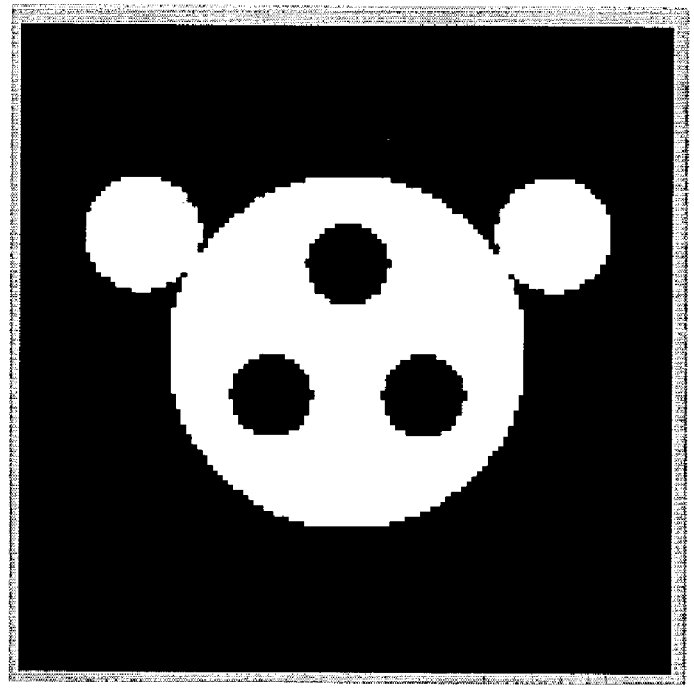
FIG. 7 is a simulated emission image.
Figure 8:
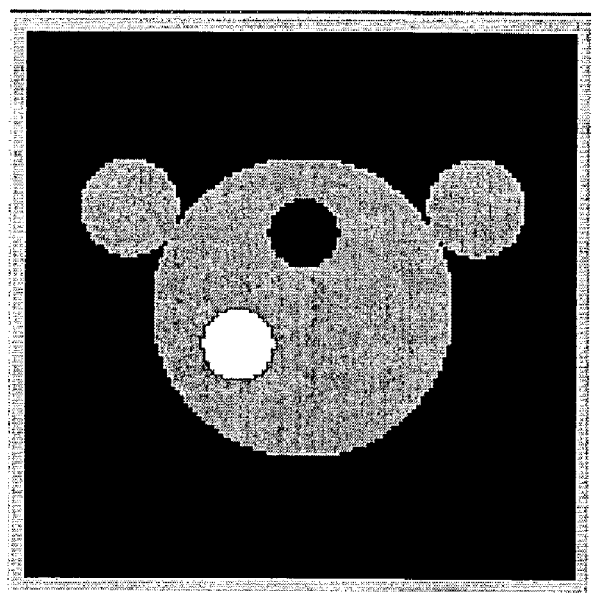
FIG. 8 is an attenuation image.

FIG. 4 illustrates a first sinogram, and FIG. 5 illustrates a second sinogram generated by shifting the first sinogram 1 millimeter (mm) shift in a Y direction. FIG. 6 illustrates a difference sinogram illustrating the differences between the first and second sinograms caused by the 1 mm shift, which represents a 1 mm sag. FIG. 7 illustrates an exemplary sinogram wherein a phantom has been imaged to illustrate the methods described herein. FIG. 8 illustrates an attenuation image of the sinogram shown in FIG. 7. In the exemplary embodiment, the phantom represents a 30 centimeter (cm) diameter "attenuation phantom" including an air insert, a non-radioactive water insert, and a Teflon insert; each insert having a diameter of approximately 7 cm. The phantom also includes two water-filled arms placed just outside the main cylinder having a 10 cm diameter. The phantom was defined on 128×128 pixels over an assumed 55 cm FOV. Projection data was generated for both the attenuation and emission images over 336 angles (in 180°). The emission sinogram was then multiplied by the attenuation sinogram. Poisson noise was added to the attenuated emission sinograms such that the total sinogram counts equaled 1.0e4, 1.0e5 and 1.0e6 total counts to allow a critique of the methods described herein at different noise levels. A second shifted sinogram shown in FIG. 5 was generated where the object was shifted by 1.07 mm (1 pixel in 512) in the y direction. The second image was generated by rebinning the 128×128 images to 512×512, shifting by 1 y pixel, and then interpolating the images back to 128×128. The shifted emission and attenuation images were then projected in the same manner as the non-shifted images. Noise was added to the attenuated, shifted sinograms. Both the non-shifted and shifted emission sinograms were then analyzed using the methods described herein with a cutoff of 0.2 and backoff of 1 pixel. For example, and referring to FIG. 9, rows 0-5 and 330-335 were averaged in both lower bound and upper bound to estimate an average x-shift per sinogram (shifted vs. non-shifted) and rows 162-173 were used to find y-shift (for sag). An average of the difference of object lower and upper bounds between shifted vs. non-shifted sinograms was then calculated. The results are shown below in Table 1. In the exemplary embodiment, the methods described herein can determine a shift of approximately ¼ pixel. In one embodiment, a plurality of filtering methods or wider bound-averaging ranges can be used to facilitate reducing image noise.

Table 1 illustrates the Y pixel-shift results for prototype evaluation using the phantom shown in FIG. 8. As illustrated the methods described herein determined a 0.25 pixel shift in Y.

TABLE 1

| sinogram | Slice counts | | |
|---|---|---|---|
| smooth | 1.00E+06 | 1.00E+05 | 1.00E+04 |
| no smooth | 2.21 | 1.58 | 0.71 |
| boxcar 3 | 0.50 | 0.38 | −2.04 |
| boxcar 5 | 0.50 | 0.25 | −2.96 |

Figure 9:
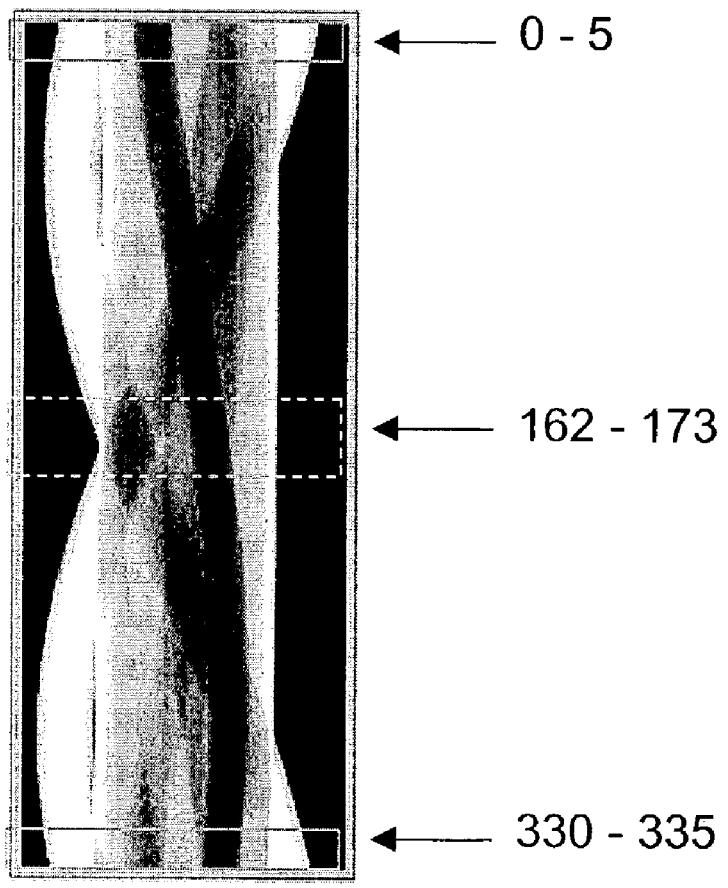
FIG. 9 is an image illustrating sinogram rows used for the method shown in FIG. 3.

FIG. 8 is a simulated emission image of a phantom, generated using the methods described herein. FIG. 9 is an attenuation image of the phantom shown in FIG. 8.

In the exemplary embodiment, the methods described can be applied following a data acquisition without operator interaction using only PET emission data, since the methods can be performed during a PET image reconstruction process. Method 60 facilitates reducing the patient-specific sag visualized in an imageset, thus improving image quality when viewing data in an orthogonal reformat manner. Additionally, the methods described herein can be made robust to noise levels in the data. For example, a sinogram smoothing, a change of cutoff threshold, and a change of sinogram row ranges can be implemented and investigated as part of an implementation.

While the invention has been described in terms of various specific embodiments, those skilled in the art will recognize that the invention can be practiced with modification within the spirit and scope of the claims.

What is claimed is:

1. A method for retrospectively correcting data prior to image reconstruction using an imaging system having a Z-axis extending longitudinally therethrough, said method comprising:
    acquiring a first sinogram of a first slice of an object at a first axial field of view at a first location with respect to the Z-axis;
    acquiring a second sinogram of the first slice of the object at a second axial field of view different than the first axial field of view, the second axial field of view at a second location with respect to the Z-axis, the second location different than the first location;
    determining at least one boundary of the object in the first sinogram and the second sinogram at the first slice;
    measuring a shift between the first sinogram and the second sinogram using the at least one determined boundary;
    assuming a linear change in the shift with respect to a slice location of the first slice at the second axial field of view;
    deducing an offset for the first slice at the second axial field of view in the second sinogram as a function of the measured shift and the assumed linear change; and
    generating a corrected image using the deduced offset for the first slice at the second axial field of view in the second sinogram to make a back projector and a forward projector, knowledgeable of an intended center for a projection.

2. A method in accordance with claim 1 wherein said acquiring a first sinogram of a first slice of an object at a first axial field of view and a second sinogram of the first slice of the object at a second axial field of view different than the first axial field of view further comprises acquiring a first sinogram of a first slice of an object at a first axial field of view and a second sinogram of the first slice of the object at a second axial field of view different than the first axial field of view using a Positron Emission Tomography (PET) system.

3. A method in accordance with claim 1 wherein said determining at least one boundary for the first sinogram and the second sinogram further comprises generating a threshold value for the first sinogram and the second sinogram.

4. A method in accordance with claim 3 wherein said generating a threshold value further comprises:
examining the first sinogram and the second sinogram to determine a maximum intensity value for at least one row of the first sinogram and a corresponding row of the second sinogram; and
setting the threshold value to equal a percentage of the maximum intensity value for the first sinogram and the second sinogram.

5. A method in accordance with claim 3 wherein said generating a threshold value further comprises:
examining the first sinogram and the second sinogram to determine a mean intensity value for at least one row of the first sinogram and a corresponding row of the second sinogram; and
setting the threshold value to equal a percentage of the mean intensity value for the first sinogram and the second sinogram.

6. A method in accordance with claim 3 further comprising traversing a row of the first sinogram and a corresponding row of the second sinogram in a first direction from a first edge of each row toward a second edge of each row to locate a pixel that has an intensity greater than the threshold value.

7. A method in accordance with claim 6 further comprising setting a boundary at the pixel that has an intensity greater than the threshold value.

8. A method in accordance with claim 6 further comprising setting a boundary at a pixel located a predetermined quantity of pixels from the pixel that has an intensity greater than the threshold value.

9. A method in accordance with claim 3 wherein said determining at least one boundary of the object in the first sinogram and the second sinogram comprises determining a right boundary and a left boundary for the first sinogram and the second sinogram.

10. A method for retrospectively correcting an image using a Positron Emission Tomography (PET) system having a Z-axis extending longitudinally therethrough, said method comprising:
acquiring a first sinogram of an object at a first axial field of view at a first location with respect to the Z-axis;
acquiring a second sinogram of the object at a second axial field of view different than the first axial field of view, the second axial field of view at a second location with respect to the Z-axis, the second location different than the first location;
generating a threshold value for the first sinogram and the second sinogram;
traversing a row of the first sinogram and a corresponding row of the second sinogram in a first direction from a first edge of each row toward a second edge of each row to locate a pixel that has an intensity greater than the threshold value;
setting a boundary at a pixel located a predetermined quantity of pixels from the pixel that has an intensity greater than the threshold value;
measuring a shift between the first sinogram and the second sinogram using the set boundary;
assuming a linear change in the shift with respect to a slice location of the first slice at the second axial field of view;
deducing an offset for the first slice at the second axial field of view in the second sinogram as a function of the measured shift and the assumed linear change; and
generating a corrected image using the deduced offset for the first slice at the second axial field of view in the second sinogram to make a back projector and a forward projector, knowledgeable of an intended center for a projection.

11. An imaging system comprising:
a radiation source;
a radiation detector configured to detect radiation emitted from said radiation source;
a longitudinal axis extending through said imaging system; and
a computer operationally coupled to said radiation source and said radiation detector, said computer configured to:
acquire a first sinogram of an object at a first axial field of view at a first location with respect to said longitudinal axis;
acquire a second sinogram of the object at a second axial field of view different than the first axial field of view, the second axial field of view at a second location with respect to said longitudinal axis, the second location different than the first location;
determine at least one boundary of the object in the first sinogram and the second sinogram;
measure a shift between the first sinogram and the second sinogram using the at least one determined boundary;
assume a linear change in the shift with respect to a slice location of the first slice at the second axial field of view;
deduce an offset for the first slice at the second axial field of view in the second sinogram as a function of the measured shift and the assumed linear change; and
generate a corrected image using the deduced offset for the first slice at the second axial field of view in the second sinogram to make a back projector and a forward projector, knowledgeable of an intended center for a projection.

12. An imaging system in accordance with claim 11 wherein, to determine at least one boundary for the first sinogram and the second sinogram, said computer is further configured to generate a threshold value for the first sinogram and the second sinogram.

13. An imaging system in accordance with claim 12 wherein, to generate a threshold value, said computer is further configured to:
examine the first sinogram and the second sinogram to determine a maximum intensity value for at least one row of the first sinogram and a corresponding row of the second sinogram; and
set the threshold value to equal a percentage of the maximum intensity value for the first sinogram and the second sinogram.

14. An imaging system in accordance with claim 12 wherein, to generate a threshold value, said computer is further configured to:
examine the first sinogram and the second sinogram to determine a mean intensity value for at least one row of the first sinogram and a corresponding row of the second sinogram; and
set the threshold value to equal a percentage of the mean intensity value for the first sinogram and the second sinogram.

15. An imaging system in accordance with claim 14 wherein said computer is further configured to set a boundary at a pixel located a predetermined quantity of pixels from the pixel that has an intensity greater than the threshold value.

16. An imaging system in accordance with claim 12 wherein said computer is further configured to traverse a row of the first sinogram and a corresponding row of the second sinogram in a first direction from a first edge of each row toward a second edge of each row to locate a pixel that has an intensity greater than the threshold value.

17. An imaging system in accordance with claim 16 wherein said computer is further configured to set a boundary at the pixel that has an intensity greater than the threshold value.

18. An imaging system in accordance with claim 12 wherein, to determine at least one boundary of the object in the first sinogram and the second sinogram, said computer is further configured to determine a right boundary and a left boundary for each of the first sinogram and the second sinogram.

19. A Positron Emission Tomography (PET) system comprising:
a radiation source;
a radiation detector configured to detect radiation emitted from said radiation source;
a longitudinal axis extending through said PET system; and
a computer operationally coupled to said radiation source and said radiation detector, said computer configured to:
acquire a first sinogram of a first slice of an object at a first axial field of view at a first location with respect to said longitudinal axis;
acquire a second sinogram of the first slice of the object at a second axial field of view different than the first axial field of view, the second axial field of view at a second location with respect to said longitudinal axis, the second location different than the first location;
generate a threshold value for the first sinogram and the second sinogram;
traverse a row of the first sinogram and a corresponding row of the second sinogram in a first direction from a first edge of each row toward a second edge of each row to locate a pixel that has an intensity greater than the threshold value;
set a boundary at a pixel located a predetermined quantity of pixels from the pixel that has an intensity greater than the threshold value;
measure a shift between the first sinogram and the second sinogram using the set boundary;
assume a linear change in the shift with respect to a slice location of the first slice at the second axial field of view,
deduce an offset for the first slice at the second axial field of view in the second sinogram as a function of the measured shift and the assumed linear change; and
generate a corrected image using the deduced offset for the first slice at the second axial field of view in the second sinogram to make a back projector and a forward projector, knowledgeable of an intended center for a projection.

20. A non-transitory computer readable storage medium encoded with a program configured to instruct a computer to:
acquire a first sinogram of a first slice of an object at a first axial field of view at a first location with respect to a longitudinal axis of an imaging system;
acquire a second sinogram of the first slice of the object at a second axial field of view different than the first axial field of view, the second axial field of view at a second location with respect to the longitudinal axis, the second location different than the first location;
determine at least one boundary of the object in the first sinogram and the second sinogram;
measure a shift between the first sinogram and the second sinogram using the at least one determined boundary;
assume a linear change in the shift with respect to a slice location of the first slice at the second axial field of view;
deduce an offset for the first slice at the second axial field of view in the second sinogram as a function of the measured shift and the assumed linear change; and
generate a corrected image using the deduced offset for the first slice at the second axial field of view in the second sinogram to make a back projector and a forward projector, knowledgeable of an intended center for a projection.

21. A non-transitory computer readable storage medium in accordance with claim 20 wherein, to determine at least one boundary for the first sinogram and the second sinogram, said program is further configured to instruct the computer to generate a threshold value for the first sinogram and the second sinogram.

22. A non-transitory computer readable storage medium in accordance with claim 21 wherein, to generate a threshold value, said program is further configured to instruct the computer to:
examine the first sinogram and the second sinogram to determine a maximum intensity value for at least one row of the first sinogram and a corresponding row of the second sinogram; and
set the threshold value to equal a percentage of the maximum intensity value for the first sinogram and the second sinogram.

23. A non-transitory computer readable storage medium in accordance with claim 21 wherein, to generate a threshold value, said program is further configured to instruct the computer to:
examine the first sinogram and the second sinogram to determine a mean intensity value for at least one row of the first sinogram and a corresponding row of the second sinogram; and
set the threshold value to equal a percentage of the mean intensity value for the first sinogram and the second sinogram.

24. A non-transitory computer readable storage medium in accordance with claim 21 wherein said program is further configured to instruct the computer to traverse a row of the first sinogram and a corresponding row of the second sinogram in a first direction from a first edge of each row toward a second edge of each row to locate a pixel that has an intensity greater than the threshold value.

25. A non-transitory computer readable storage medium in accordance with claim 24 wherein said program is further configured to instruct the computer to set a boundary at the pixel that has an intensity greater than the threshold value.

26. A non-transitory computer readable storage medium in accordance with claim 24 wherein said program is further configured to instruct the computer to set a boundary at a pixel located a predetermined quantity of pixels from the pixel that has an intensity greater than the threshold value.

27. A non-transitory computer readable storage medium in accordance with claim 21 wherein, to determine at least one boundary of the object in the first sinogram and the second sinogram, said program is further configured to instruct the computer to determine a right boundary and a left boundary for each of the first sinogram and the second sinogram.

* * * * *